United States Patent [19]

Saville

[11] Plant 5,031

[45] Apr. 12, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 307,379

[22] Filed: Oct. 1, 1981

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of orange red and yellow coloring borne singly and in large sprays.

1 Drawing Figure

The present invention relates to a new and distinct variety of rose plant of the miniature rose class, which was originated by my crossing as seed parent the rose known as "Rise 'N Shine" (U.S. Plant Pat. No. 4,231) and the rose known as "Sheri Anne" (U.S. Plant Pat. No. 3,826) as pollen parent.

Among the novel characteristics possessed by this new variety which distinguish it from its parents and all other varieties of which I am aware are flowers of unusual multi-coloring borne singly and in large sprays. Flowers are yellow and orange red with darker orange red colored distinct petal edge section and pale yellow lower petal section toward point of attachment. The orange red color darkens before fading. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.). The terminology used in color description herein refers to plate numbers in the aforementioned color chart, e.g., "22B" is plate 22B of The Royal Horticultural Society Color Chart.

Parentage: Seedling.

*Seed parent.*—"Rise 'N Shine".

*Pollen parent.*—"Sheri Anne".

Class: Miniature.

The following observations are made of specimens grown outdoors in Essex County, Mass. during the month of July.

FLOWER

Blooming habit: Continuous, very profuse.

A. Bud:

(1) *Size.*—Small.

(2) *Form.*—Ovate, long pointed.

(3) *Color.*—When sepals first divide — pale yellow. Orange red petal edge while sepals are still raised.

(4) *Sepals.*—Slightly foliated, slightly longer than bud, smooth edges (5) *Peduncle.*—Length — ½ to ¾ inch. Aspect — straight. Strength — erect. Color — 138B.

B. Bloom:

(1) *Size.*—Average size when fully expanded — about ⅞ to 1 inch.

(2) *Borne.*—Singly and sprays.

(3) *Form.*—High centered at first opening quickly to flat blooms.

(4) *Petalage.*—Number of petals under normal conditions — about 25 to 30.

(5) *Color.*—Pale yellow buds with orange red petal edges open into multi-colored blooms sometimes deep yellow 22B to C on petal undersurface lightening to paler yellow. Petal top surface has orange red 32B coloring from petals edge inward becoming pale yellow at about ⅔ of petal length. Open blooms show deep yellow center combining pale yellow petal coloring with deep yellow stamens. As blooms age, orange red coloring deepens to 32A before fading to 37A.

C. Petals:

(1) *Texture.*—Medium.

(2) *Appearance.*—Satiny.

(3) *Form.*—Spatulate oval.

(4) *Arrangement.*—Regularly arranged shingle-like.

(5) *Petaloids in center.*—Few.

(6) *Persistence.*—Drop off cleanly.

(7) *Fragrance.*—Slight.

(8) *Lasting quality.*—Average.

REPRODUCTIVE ORGANS

A. Stamens, filaments and anthers:

(1) *Arrangement.*—Stamens regular, arranged around styles.

(2) *Color.*—13B.

B. Pollen:

*Color.*—14B.

C. Styles: Even, moderate length.

D. Stigmas:

*Color.*—1D.

E. Hips: None observed.

PLANT

A. Form: Compact, bushy.

B. Growth: Very vigorous, free branching.

*Height attained.*—About 4 to 10 inches.

C. Foliage: Compound 5 to 7 leaflets.

(1) *Size.*—Small.

(2) *Quantity.*—Abundant with short internodes.

(3) *Color.*—New foliage: Upper side — near 137B. Under side — near 138C. Old foliage: Upper side — near 147A. Under side — near 138B.

(4) *Shape.*—Oval, pointed.

(5) *Texture.*—Upper side is glossy and under side is flat.

(6) *Edge.*—Serrate.

(7) *Serration.*—Deeper toward apice.

(8) *Leaf stem.*—Color — near green with wine red cast.

(9) *Stipules.*—Medium, simple, smooth.

(10) *Resistance to disease.*—Blackspot — average. Mildew — average. Rust — average.

D. Wood:

(1) *New wood.*—Color — near 148B. Bark — smooth.

(2) *Old wood.*—Color — near 141A. Bark — smooth.

E. Thorns:

(1) *Thorns.*—Quantity (main stalk): few On laterals from stalk — none. Form — long pointed, thin, slightly angled downward. Length — small. Color — near 182B. Position — irregular.

(2) *Prickles.*—None.

F. Winter hardiness: Average hardiness.

I claim:

1. A new and distinct variety of rose plant of the miniature class, substantially as shown and described, characterized by flowers of orange red and yellow coloring darkening before fading and borne singly as well as in large sprays.

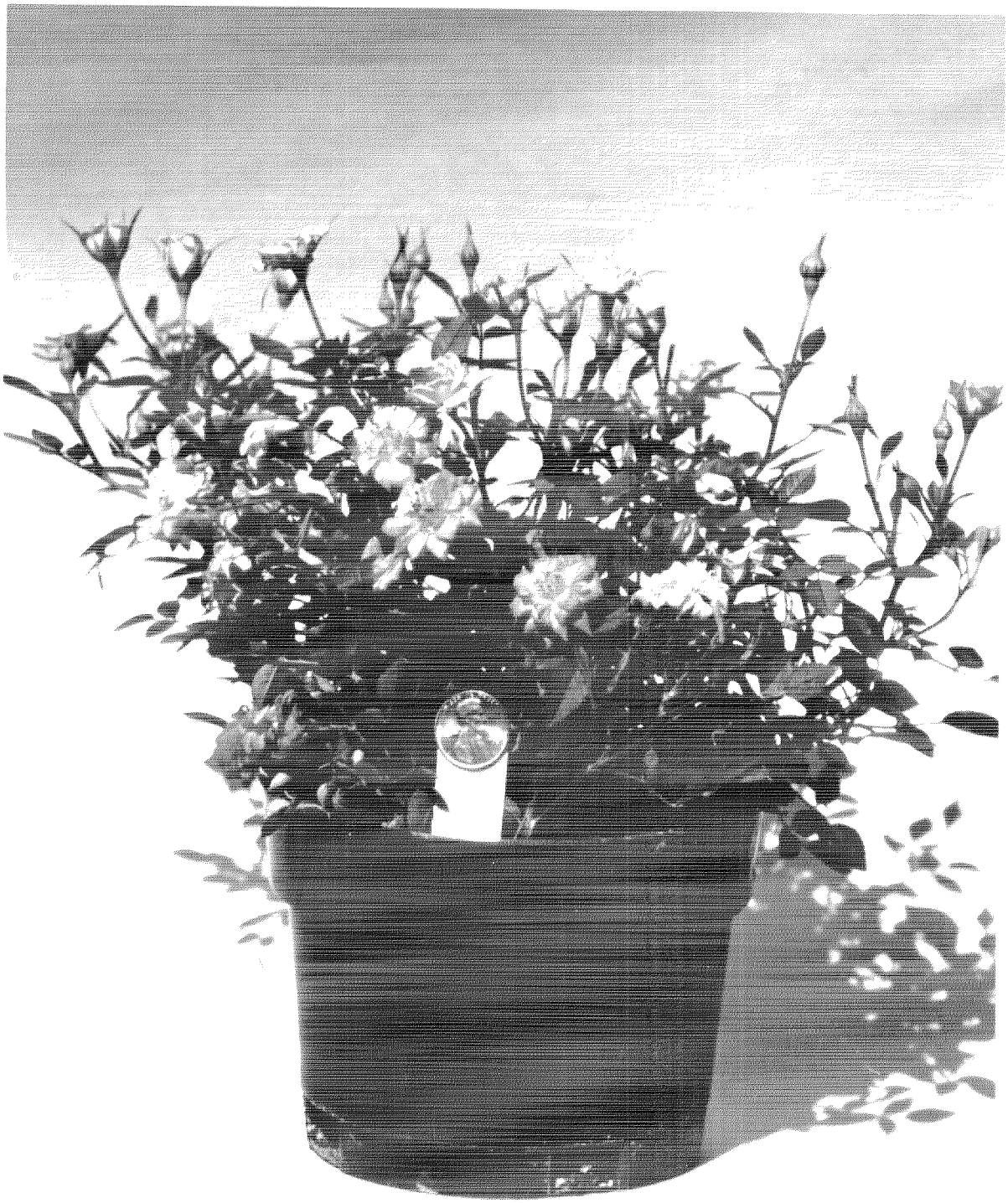

* * * * *